United States Patent [19]
Quistgaard

[11] Patent Number: 5,485,842
[45] Date of Patent: Jan. 23, 1996

[54] ULTRASONIC DIAGNOSTIC SCAN CONVERSION FOR THREE DIMENSIONAL DISPLAY PROCESSING

[75] Inventor: Jens U. Quistgaard, Seattle, Wash.

[73] Assignee: Advanced Technology Laboratories, Inc., Bothell, Wash.

[21] Appl. No.: 347,028

[22] Filed: Nov. 30, 1994

[51] Int. Cl.⁶ ............................................. A61B 8/00
[52] U.S. Cl. ............................. 128/66.07; 128/916
[58] Field of Search .................... 382/6; 364/413.13, 364/413.22–413.25, 518; 128/660.07, 916

[56]         References Cited
        U.S. PATENT DOCUMENTS

| | | |
|---|---|---|
| 4,581,636 | 4/1986 | Blaker et al. . |
| 4,694,434 | 9/1987 | von Ramm et al. . |
| 4,737,921 | 4/1988 | Goldwasser et al. ........... 364/518 |
| 4,985,834 | 1/1991 | Cline et al. .................. 364/413.22 |
| 5,159,931 | 11/1992 | Pini . |
| 5,227,969 | 7/1993 | Waggener et al. ............. 364/413.26 |
| 5,280,428 | 1/1994 | Wu et al. ..................... 364/413.13 |
| 5,282,471 | 2/1994 | Sato .............................. 128/660.07 |
| 5,295,486 | 3/1994 | Wollschlager et al. ......... 128/660.01 |
| 5,295,488 | 3/1994 | Lloyd et al. ................... 128/653.1 |
| 5,315,512 | 5/1994 | Roth . |
| 5,329,929 | 7/1994 | Sato .............................. 128/660.65 |
| 5,331,552 | 7/1994 | Lloyd et al. ................... 364/413.15 |
| 5,353,354 | 10/1994 | Keller et al. .................. 382/6 |

OTHER PUBLICATIONS

"V–Buffer: Visible Volume Rendering" by C. Upson et al. in Computer Graphics, vol. 22, No. 4 (Aug. 1988), pp. 59–64.
*Computer Graphics, Principles and Practice* by J. D. Foley et al., Addison–Wesley Pub. Co., (1987), at sec. 5.6.

*Primary Examiner*—Francis Jaworski
*Attorney, Agent, or Firm*—W. Brinton Yorks, Jr.

[57]         ABSTRACT

A method and apparatus are provided for processing ultrasonic diagnostic image information acquired in a plurality of scan planes for presentation as a three dimensional display of a volumetric region of the body. The image points in each scan plane are repositioned by approximating the rotation and translation of the scan plane in correspondence with the angle from which the volumetric region is to be viewed. This approximation is accomplished using conventional scan conversion processors by scaling the spatial coordinates of the original ultrasonic image in one or more dimensions and translating the image in one or more directions in correspondence with the viewing angle. A plurality of such scaled and translated images are accumulated and displayed in a combined three dimensional image presentation.

24 Claims, 8 Drawing Sheets

ULTRASONIC DIAGNOSTIC SCAN CONVERSION FOR THREE DIMENSIONAL DISPLAY PROCESSING

This invention relates to improvements in ultrasonic diagnostic imaging techniques, and in particular to ultrasonic signal processing of planar image information for presentation in a three dimensional image format.

Various methods and devices have been proposed for ultrasonically scanning a volume within a subject for three dimensional analysis and display. Many of these techniques involve the scanning of a number of spatially adjacent image planes. The ultrasonic information from these associated planes can be analyzed and displayed on the basis of spatial coordinates of the data within a plane, and on the basis of the spatial relationship of each plane to the others. The information can be displayed in a three dimensional image format such as a perspective view of the volume being imaged. Effective three dimensional images can be formed by displaying a series of spatially related two dimensional images together in various overlapping and aligned relationships. U.S. Pat. No. 5,353,354, for instance, describes the acquisition and display of a number of parallel ultrasonic image planes, and a technique for displaying two intersecting image planes.

A number of scanning techniques utilizing specially devised scanning devices have been proposed for acquiring these spatially related image planes. The article "Three-Dimensional Reconstruction of Echocardiograms Based On Orthogonal Sections," by S. Tamura et al. *Pattern Recognition,* vol. 18, no. 2, pp 115–24 (1985) discusses three such devices: a guide rail to guide an ultrasonic probe while acquiring parallel image planes; a jointed arm in which sensors in the arm joints provide spatial coordinates for the transducer; and rotation of a transducer about the cardiac long axis. A rotating transducer probe for the latter purpose is shown and described in "Multidimensional Ultrasonic Imaging for Cardiology," by H. McCann et al., *Proceedings of the IEEE,* vol. 76, no. 9, pp 1063–73 (Sept. 1988). It would be preferable, however, to be able to acquire multiple image planes for three dimensional presentation without the need for special scanning devices or apparatus.

When the principles of two dimensional ultrasonic imaging are extended into a third dimension, there is generally a significant increase in the signal and image processing complexity accompanied by a corresponding increase in hardware and software complexity and expense. The extension into the third dimension is therefore generally considered to entail the development of more complex and expensive ultrasound system architectures. It is desirable to provide three dimensional ultrasonic imaging capability with only modest increases in ultrasound system complexity and expense. In particular, it is desirable to be able to afford three dimensional ultrasonic imaging capability using the hardware of a conventional two dimensional ultrasonic imaging system.

In accordance with the principles of the present invention, three dimensional ultrasonic imaging is made possible using conventional two dimensional ultrasonic imaging hardware through novel use of the scan converter of the ultrasound system. A plurality of two dimensional images are acquired. The images are processed through scan conversion to approximate their rotation to various image planes and projection back to a reference plane such as the original image plane. This process may be performed using conventional scan conversion hardware to rescale the sector angle or depth of sector images, or the aspect ratio of rectangular images. In a preferred embodiment projections are made from a plurality of planes for each image, then stored in a sequence of combined images, wherein each combined image comprises a set of corresponding projected images offset with respect to each other. Each combined image is a different view of a three dimensional region occupied by the planar image information. The sequence of combined images can be replayed on a display to depict the three dimensional region as if it is rotating in front of the viewer. The stored combined images can be recalled on the basis of the three dimensional viewing perspectives and displayed sequentially in a three dimensional presentation. This technique can utilize manual scanning and conventional scan conversion hardware so as to quickly and easily enable a user to perform three dimensional ultrasonic imaging.

Figure 1:
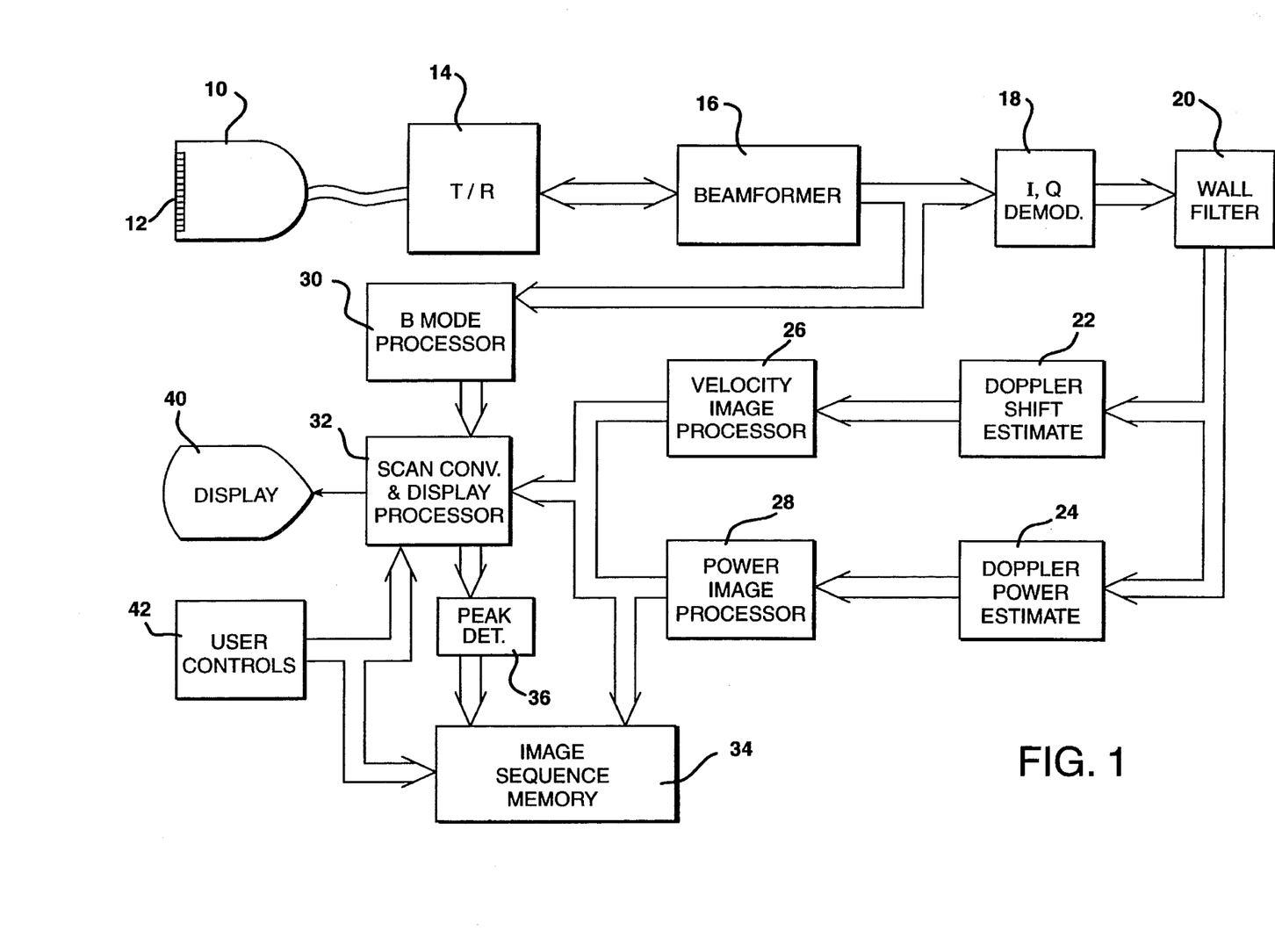
FIG. 1 is a block diagram of an ultrasonic diagnostic imaging system constructed in accordance with the principles of the present invention.

Referring first to FIG. 1, a block diagram of an ultrasonic diagnostic imaging system constructed in accordance with the principles of the present invention is shown. An ultrasonic probe 10 includes a multielement transducer 12 which transmits waves of ultrasonic energy into the body of a patient and receives ultrasonic echoes returning from structures and in the body. In the case of ultrasonic wave transmission for Doppler interrogation of the body, it is the echoes returning from moving tissue, blood and other fluids in the body that are of interest. The ultrasonic probe 10 is connected to a transmitter/receiver 14 which alternately pulses individual elements of the transducer to shape and steer an ultrasonic beam, and receives, amplifies and digitizes echo signals received by the transducer elements following each pulse transmission.

The transmitter/receiver 14 is coupled to a beamformer 16 which controls the times of activation of specific elements of the transducer 12 by the transmitter/receiver. This timing enables the transducer 12 to transmit a shaped and focused ultrasound beam in a desired direction. The beamformer 16 also receives the digitized echo signals produced by the transmitter/receiver during echo reception and appropriately delays and sums them to form coherent echo signals.

The echo signals produced by the beamformer 16 are coupled to a B mode processor 30 and an I,Q demodulator 18. The B mode processor processes the amplitude information of the echo signals on a spatial basis for the formation of a structural image of the tissue in the area of the patient being scanned. The I,Q demodulator 18 demodulates the received echo signals into quadrature components for Doppler processing. The I,Q components are filtered by a wall filter 20 to remove low frequency artifacts stemming from the movement of vessel walls or other tissue in applications where it is only the motion of flowing fluids such as blood that is of interest. The filtered I,Q components are then applied to a Doppler shift estimation processor 22 and a Doppler power estimation processor 24.

The Doppler shift estimation processor 22 operates to estimate a Doppler phase or frequency shift from the I,Q components at each sample volume location of the image field. The Doppler shift estimation processor operates on a number of signal samples resulting from the interrogation of each sample volume location by an ensemble of Doppler interrogation pulses. The sample volume values are applied to a velocity image processor 26 which maps the values to color values for display. The color values are applied to a scan converter and display processor 32 operated in accordance with the principles of the present invention which spatially organizes the color values for three dimensional display as discussed below. The color values are displayed as pixels on a display 40, wherein each color represents a particular velocity of flow in a particular direction at that pixel location. The color flow velocity information is conventionally overlaid with a structural image of the interior of the body made possible by the structural information provided by the B mode processor 30. This compound image shows both the direction and velocity of blood flow, as well as the structure of the vessels or organs which contain the flowing blood.

The Doppler power estimation processor 24 estimates the Doppler signal power from the I,Q signal components at each sample volume location using the expression $(I^2+Q^2)^{1/2}$. The Doppler power estimates at each location can be processed and displayed in real time or can be averaged with earlier acquired power estimates for each location. In a preferred embodiment, each sample volume location is interrogated by a number of pulses and the estimation processor 24 utilizes the signals obtained from all interrogations in the estimations of Doppler power at the sample volume locations. These Doppler power estimates are mapped to display intensity or color values by a power image processor 28. The display values with their spatial coordinates are stored in separate planar images in an image sequence memory 34 and are also applied to the scan converter and display processor 32 which spatially arranges the Doppler power display values in the desired image format, e.g., sector or rectangular. The two dimensional Doppler power images may then be displayed on a display 40 or recalled from the image sequence memory 34 for three dimensional processing using peak detection to produce maximum Doppler power intensity images as discussed in copending U.S. patent application No. 08/343,811, entitled "ULTRASONIC DIAGNOSTIC SCANNING FOR THREE DIMENSIONAL DISPLAY" filed Nov. 22, 1994. User operation of the system of FIG. 1 is effected through various user controls 42 which enable the user to select the type of imaging to be performed, i,e,, B mode, color velocity Doppler or Doppler power imaging, and to store and retrieve images from the image sequence memory 34 for three dimensional display, for example.

Figure 2:
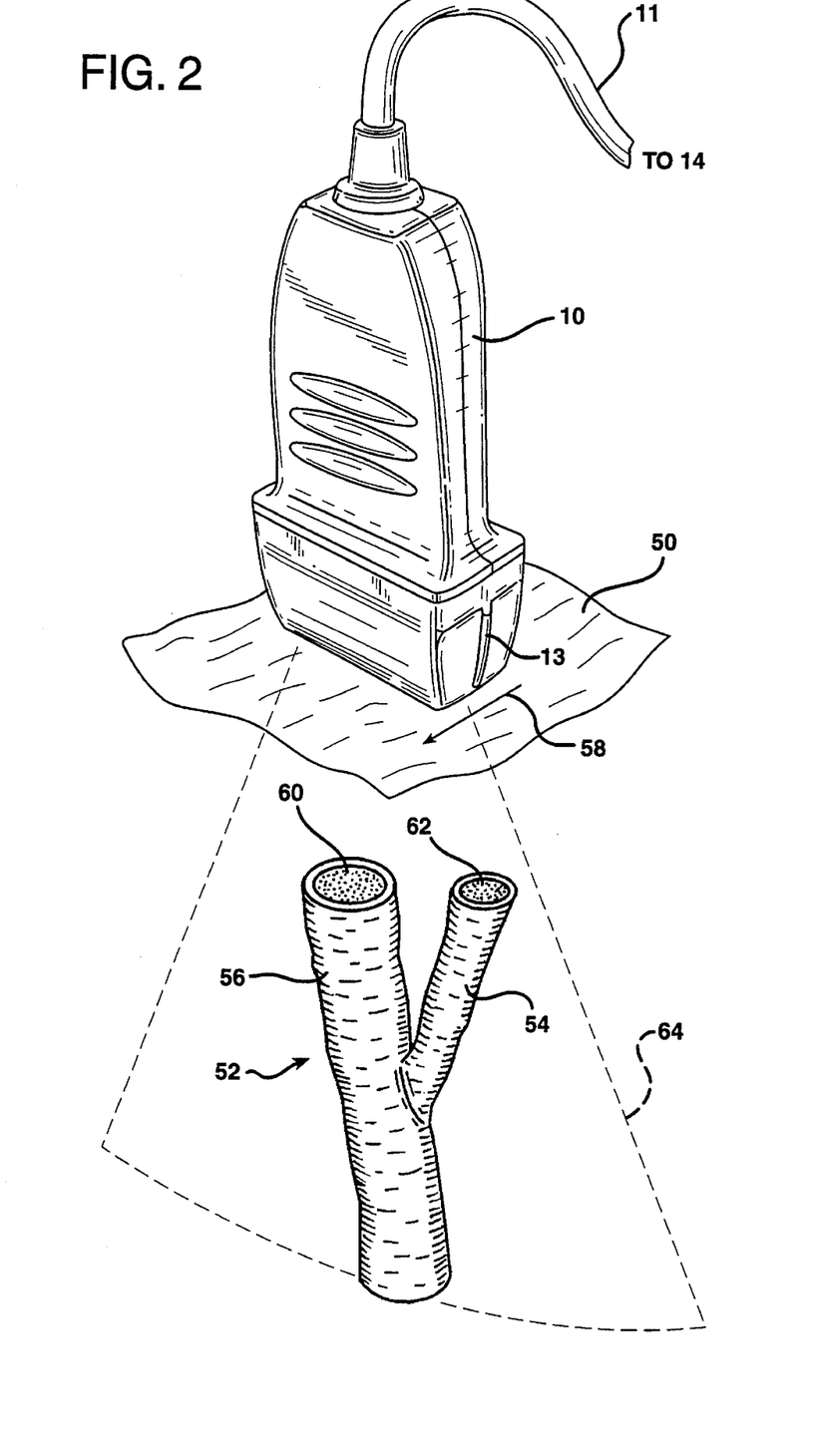
FIG. 2 illustrates the manual scanning of a bifurcation in the body of a patient.

FIG. 2 illustrates the use of the ultrasonic probe 10 to manually acquire a sequence of image planes for three dimensional display. A portion of the probe cable 11 leading to the transmitter/receiver of the ultrasound system is shown at the top of the probe. The transducer aperture of the probe 10 is in contact with the skin of the patient over the region of the body which is to be scanned. The skin of the patient is represented by a layer 50 in the drawing. In this example the region of the patient being scanned includes a blood vessel bifurcation 52 having a small vessel 54 branching out from a larger vessel 56. Blood is flowing inside the structural walls of the vessels as indicated at 60 and 62.

The bifurcation 52 may be scanned by rocking or fanning the probe 10 while in contact with the patient. In a preferred technique the probe aperture slides over the skin 50 as indicated by arrow 58 to scan the bifurcation region with a plurality of parallel image planes. One such image plane 64, here shown as a sector, is seen projecting from the transducer aperture of the probe. The relation of the image plane 64 to the probe is denoted by an image plane marker 13 on the side of the probe case. The marker 13 is in the same plane as the image plane 64, and denotes the upper left side of the image in its uninverted display orientation.

In accordance with the present invention, the ultrasound system acquires and processes ultrasonic signal information from a plurality of image planes as the probe slides over the bifurcation region of the patient as indicated by the arrow 58. The duration of such a scan can typically last about ten to twenty seconds, during which time 100 to 200 image planes are acquired, processed and stored in the image sequence memory 34.

Figure 3A:
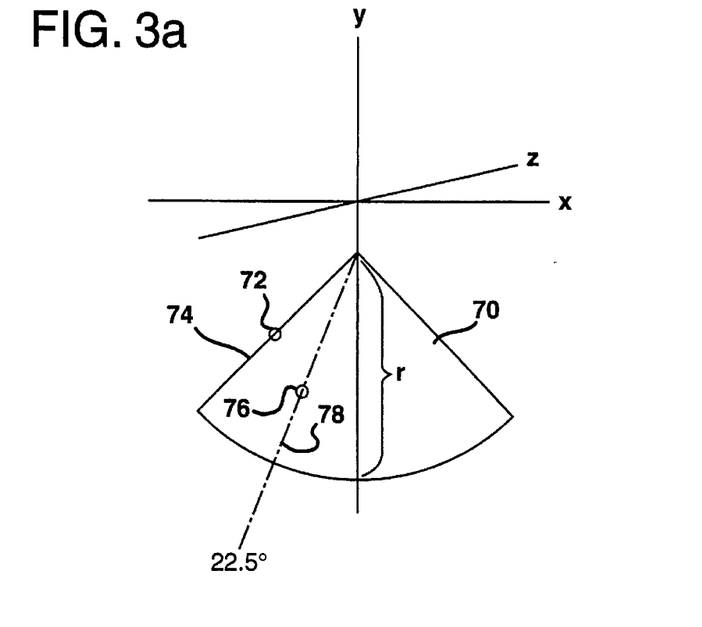
FIGS. 3a–3d illustrate principles of the present invention by which conventional two dimensional scan conversion processors can be controlled to process sector images for three dimensional image presentation.

The scan converter and display processor 32 processes the image planes in accordance with the present invention as illustrated in the following drawings. FIG. 3a illustrates a 90° sector scanned image 70, which is formed from a plurality of scan lines radiating from an apex over an angle of 90°. One image point 72 is shown on the leftmost scan line 74 of the sector image and another image point 76 is shown on the scan line 78. The scan line 78 is at an angle of 22½° which is halfway across the left half of the sector. In FIG. 3a the 90° sector image 70 is located in the x-y plane. The sector image 70 is used with the other, similarly acquired image planes in a combined three dimensional presentation which is a view of the region containing the plane along a viewing line in a horizontal plane which is normal to the x-y plane. The sector image 70 and the other planar images of this presentation may be individually processed by the scan converter and display processor 32 to convert their polar coordinates to a system of Cartesian coordinates in the usual manner in which two dimensional sector images are processed.

The sector image 70 and its companion planes may be processed for three dimensional presentation by relocating points in the images in order to present the images as if the scanned region is being viewed from directions other than orthogonal to the image planes. A mathematically precise expression for relocating the image points when viewing the scanned region from different viewpoints in the horizontal plane is:

$$\begin{bmatrix} x' \\ y' \end{bmatrix} = \begin{bmatrix} x\cos(\theta) \\ y \end{bmatrix} + \begin{bmatrix} z\sin(\theta) \\ 0 \end{bmatrix}$$

where θ is the angle of rotation of the image in relation to a reference plane such as a viewing plane orthogonal to the line of sight of a viewer, x, y and z are the coordinates of a point in the original image plane, and x' and y' are the coordinates of the image point after relocation. The z coordinate of a planar image may be obtained by assuming a nominal spacing between image planes or by acquiring a measured spatial coordinate of each plane as described in the copending U.S. patent application mentioned above. The present invention is premised on the recognition that when this expression is in the form shown above, the left term is a pure image rotation term and the right term is a pure image translation term. The separability of the two terms means that rotation and translation processing can be performed separately, affording simplicity in processing.

Point relocation when viewing the scanned region from different viewpoints in a vertical direction is expressed by:

$$\begin{bmatrix} x' \\ y' \end{bmatrix} = \begin{bmatrix} x \\ y\cos\theta \end{bmatrix} - \begin{bmatrix} 0 \\ z\sin\theta \end{bmatrix}$$

where the first term after the equal sign is the rotation term and the second term is the translation term.

Point relocation for views of the scanned region as it is rotated about a z axis is performed by the expression:

$$\begin{bmatrix} x' \\ y' \end{bmatrix} = \begin{bmatrix} x\cos\theta - y\sin\theta \\ x\sin\theta + y\cos\theta \end{bmatrix}$$

which, by its single term form, is seen not to possess the separability of the previous two expressions. In this expression θ is the degree of rotation of the planes about a z axis relative to a reference direction.

Figure 3B:
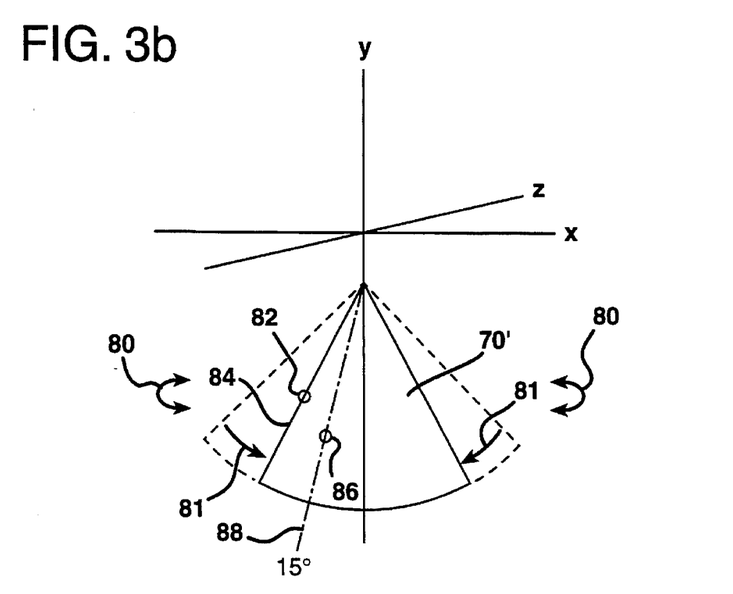
Figure 3C:
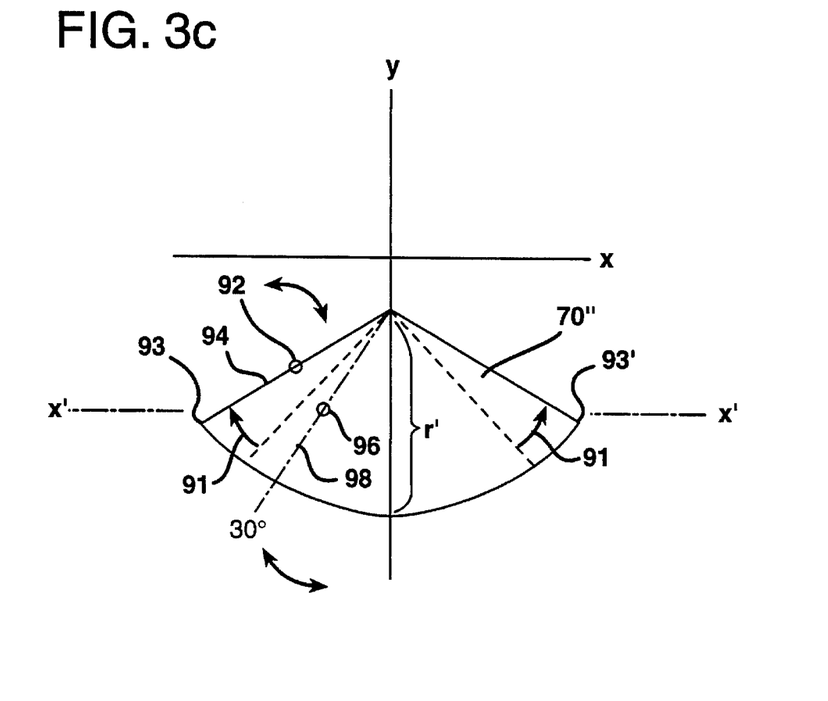

In accordance with the present invention the above mathematical expressions are approximated by control of the scan converter and display processor 32 as shown in FIGS. 3b and 3c. When the scanned region is to be viewed from an angle in the horizontal plane other than orthogonal to the x-y plane, the processing technique of FIG. 3b is employed. The sector image is processed as if it has rotated about the y axis as indicated by arrows 80 from the x-y plane to a new y-z plane, then is projected back to the viewing plane seen by the viewer. When projected back the sector appears to span a narrower sector angle, and in FIG. 3b the sector angle has decreased from the original 90° sector shown by the dashed sector outline to a new, narrower angled sector 70' as indicated by the arrows 81 in the drawing. In this drawing the sector 70' spans an angle of 60°. The same image information of the sector image 70 is converted from polar to Cartesian coordinates by the scan converter and display processor 32, but this time over a 60° sector angle. The scan lines of the sector image 70' are thus closer together than the scan lines of the sector image 70 of FIG. 3a. The point 72 of FIG. 3a is still located on the leftmost scan line 84 and the point 76 is still located on a scan line halfway across the left half of the sector, but now on a scan line at an angle of 15° in this example.

The present inventor has found that this process of rotating an image plane about an axis and projecting the rotated plane back to the viewing plane can be effectively approximated in an ultrasonic diagnostic imaging system by scaling the original ultrasonic image in one or more dimensions. In FIG. 3b the scan line spacing of FIG. 3a is rescaled so that the scan lines are presented over a 60° sector instead of the original 90° sector. Several significant advantages result from this finding. One is that the image can be processed for three dimensional display with conventional two dimensional image scan conversion hardware. Another advantage is that one processed image can be used twice, once for the y-(+z) plane and again for the y-(-z) plane, the plane the sector would be in if rotated about the y axis by the same amount but in the opposite direction. This advantage stems from the inventor's recognition that the first two expressions given above are separable into two terms, a rotational term and a translational term, and that only a single coordinate is variable in the translational term. Thus, three dimensional image processing time is halved. Once the rotated image planes have been processed for half of the desired span of viewing planes, the same processed images are used for the remaining viewing planes. Translation of the rotated image planes is performed in a single direction for each axial rotation, depending on the direction of rotation. Finally, a major advantage is realized in the simplicity of the processing used to perform the scaling, from both a control software and a time of execution points of view.

In addition to considering the viewing planes as if the scanned region is turning horizontally in front of a viewer, the subject of the example of FIG. 3b, image planes can be processed as if the scanned region is turning in a vertical plane. For views from these angles the information of the sector image 70 is processed as if the sector is rotated about a midline x'-x' in FIG. 3c, then projected back onto the viewing plane. This projection results in the image information being scaled by the scan converter and display processor 32 for compression in the vertical direction. The sector information is processed with a radial depth r' which is less than the radial depth r of the original sector, and the sector angle is broadened as indicated by the arrows 91 extending from the dashed boundaries of the original sector to the new sector boundaries. While the angle of the sector broadens, the lateral width of the sector does not change; the horizontal distance between the two most lateral extensions of the sector, from 93 to 93' in FIG. 3c, remains constant. The point 72 in the original sector is displayed on the outermost scan line 94 of the sector 70", and the point 76 becomes point 96 on scan line 98, still halfway across the left half of the sector 70" but this time at an angle of 30° in this example.

By virtue of this rescaling technique, the advantages cited above continue to apply. The image information can be processed by standard scan converter hardware and each processed sector image 70" can be used twice, one for a viewing angle from above and again for the complementary viewing angle from below. The processing can be done quickly and with relatively simple control software.

Figure 3D:
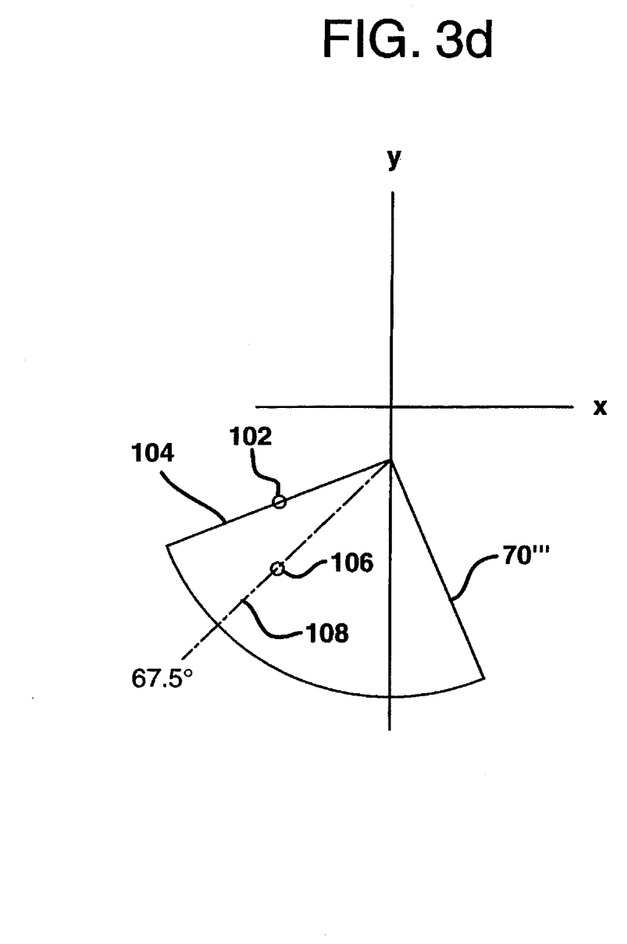

A third possibility is rotation of the scanned region about the viewing line extending from the observer to the scanned region. This change in view is accommodated by effectively rotating the original sector image 70 about its apex to a different angular position as illustrated by sector image 70''' in FIG. 3d. The sector image 70''' still occupies 90° but instead of spanning a range from +45° to -45° with respect to the y axis as shown in FIG. 3a, the sector spans a different 90° range such as the illustrated range of +135° to -45° as shown in FIG. 3d. Original display point 72 has been relocated as point 102 on the leftmost scan line 104, and the scan line 78 has moved to an angle of 67½° relocating point 76 to point 106. This processing continues to offer one of the previous advantages which is that the processing can be performed by the same scan conversion hardware, but it will be apparent that each rotated image will be used only once, not twice as before. The symmetry of the rotation about the scan plane apex does afford a simplification of control software, however, as rotation in one direction can be effected in the complementary direction by a change of sign.

Figure 4A:
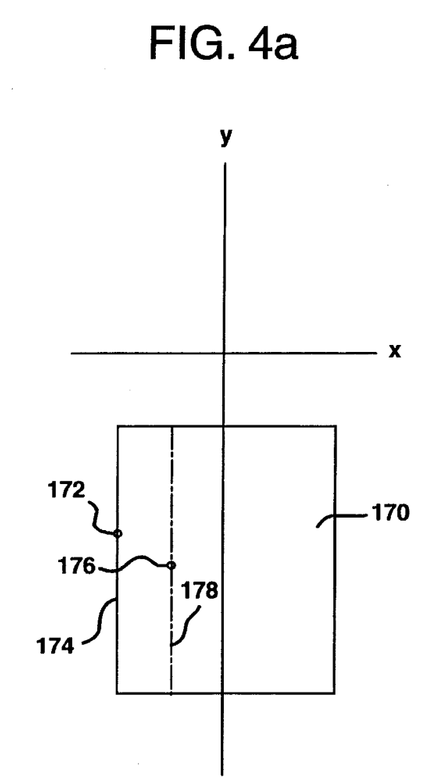
FIGS. 4a–4d illustrate principles of the present invention by which conventional two dimensional scan conversion processors can be controlled to process linear scanned images for three dimensional image presentation.
Figure 4B:
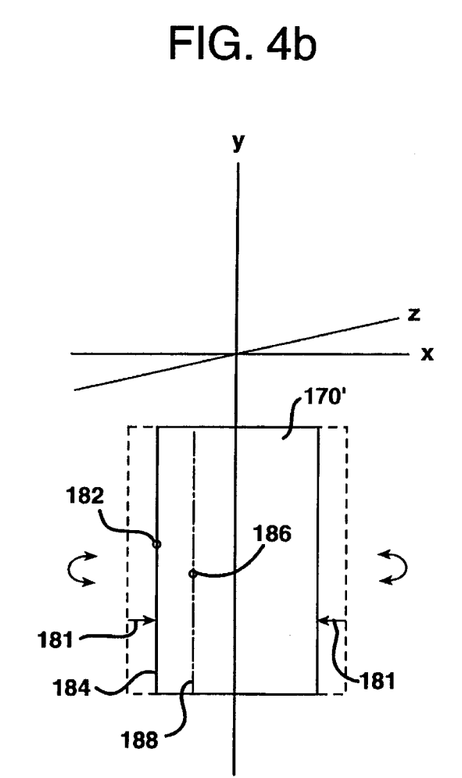

The inventive three dimensional image processing technique is also applicable to linear scanned image planes in which the scan lines are arrayed in parallel rather than radially. FIG. 4a illustrates a rectangular image 170 located in the x-y plane and centered about the y axis. A point 172 is reproduced on the leftmost scan line 174 of the image and a point 176 is located on a scan line 178 which is halfway between the center of the image and the leftmost scan line 174. For reproduction of the image as if rotated about the y axis to a position in the y-z plane as shown in FIG. 4b, the rotated image is effectively projected back onto the viewing plane and reproduced with a compressed width by rescaling the image in the x direction; the scan lines are closer together in the image 170' than they were in the original image 170. This width compression is indicated by the inward pointed arrows 181 between the dashed outline of the original image 170 and the lateral boundaries of the image 170'. The point 172 is still positioned on the leftmost scan line 184 at the same image depth, but has moved inward with the scan line and is shown as point 182. Likewise the point 186 is still on the scan line 188 halfway between the center of the image and the leftmost scan line 184, but has moved laterally with the rescaling of the scan line spacing.

Figure 4C:
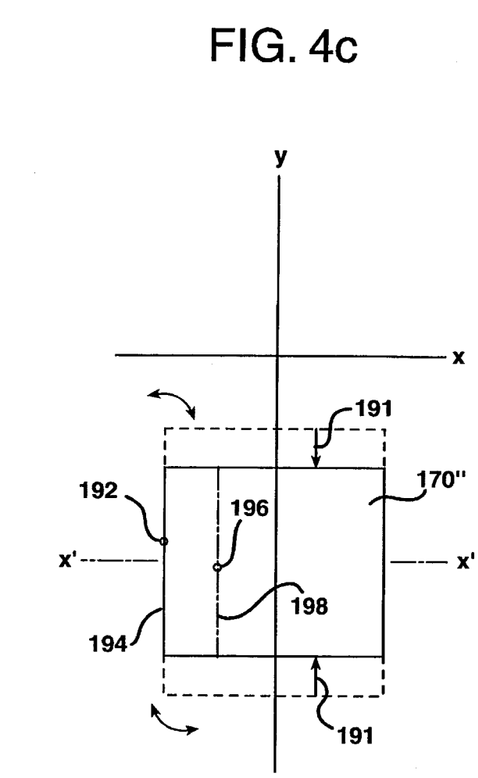

In FIG. 4c the image 170 is effectively rotated about the midline x'-x' and projected back onto the viewing plane for use when viewing a three dimensional volume from above or below its horizontal center plane. The arrows 191 are drawn inward from the dashed outline of the original image to show that the image 170" has been compressed vertically in comparison with the original image by rescaling the original image scan lines in the y direction. The point 192 on the leftmost scan line 194 is reproduced closer to the axis x'-x' than was the case for point 172 of the original image, as is true for point 196 by reason of the vertical compression. The horizontal positions of these points remain the same, as the horizontal coordinates of the image points are unchanged in comparison with the original image.

Figure 4D:
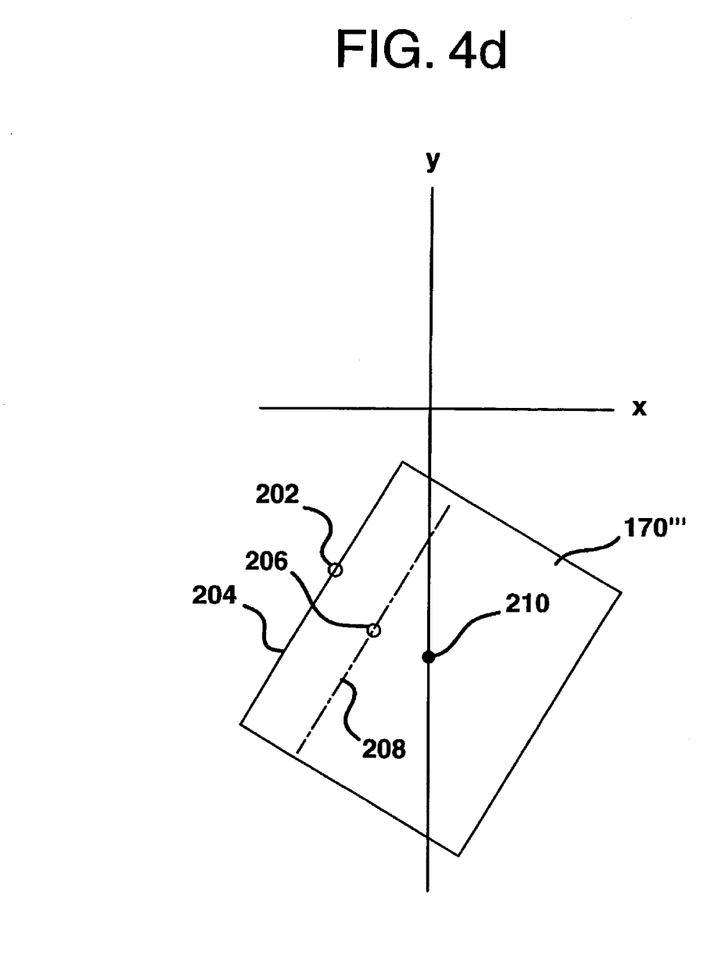

In FIG. 4d the original image is rotated about its center point 210. The rotated image 170''' is otherwise dimensionally the same as the original image, with only the angle of the scan lines changing.

The rectangular image processing technique has the same advantages as discussed above for the inventive sector image processing. Standard two dimensional scan conversion hardware can be used and the rotated images of FIGS. 4b and 4c can be utilized twice for three dimensional perspective views from complementary angles relative to the orthogonal direction. The processing of FIGS. 4b and 4c is done by simple rescaling of the image information in either the x or the y direction.

Figure 5A:
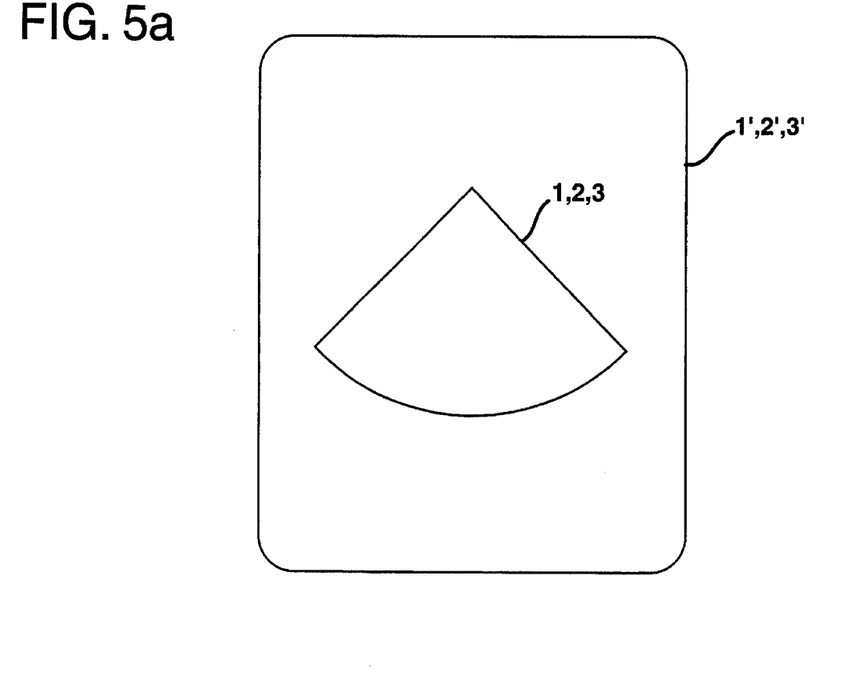
FIGS. 5a–5d illustrate the translation of a groups of ultrasonic image planes processed for three dimensional presentation in accordance with the principles of the present invention.

After the image information has been rotated about the three axes as shown in FIGS. 3a–3d and 4a–4d, a plurality of correspondingly rotated images are displayed simultaneously in a combined image. For example, if a sequence of 100 90° sector images was acquired and each image in the sequence was converted to a 60° sector image as illustrated by FIG. 3b, the 100 60° images are presented in a combined display. For an effective three dimensional presentation the images are translated in correspondence with their degree of rotation and interplane spacing and hence in correspondence with the viewing angle of an observer. For example, FIG. 5a illustrates a group of three planar 90° sector images aligned without translation. This combination of images is a presentation of the three planar images as the imaged region would appear when viewed along an axis normal to the plane of the drawing. The three sector images 1, 2, and 3 are all aligned on top of each other, as are the three image frames 1', 2', and 3' which are shown for reference purposes.

Figure 5B:
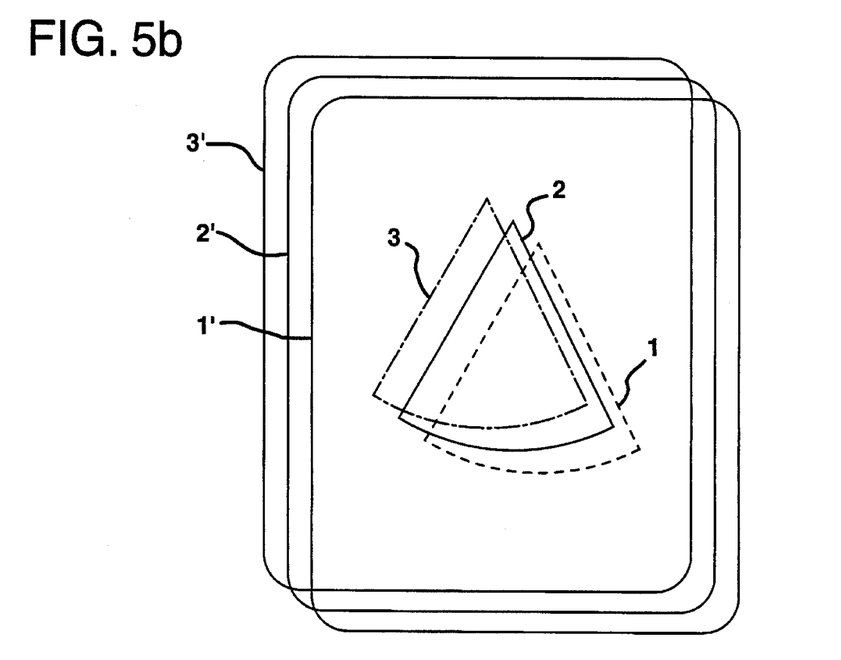
Figure 5C:
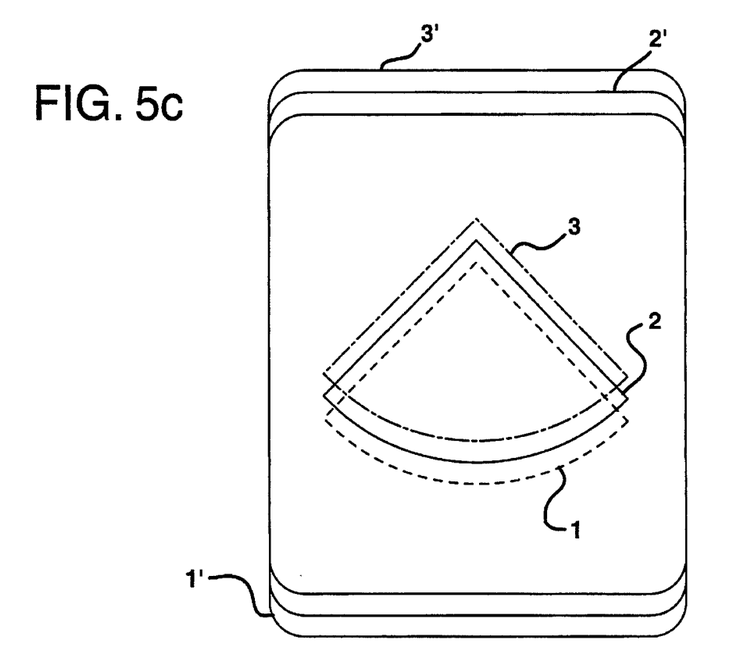

In FIG. 5c the three sector images have been translated vertically, as if the viewer is viewing the scanned region from above its central horizontal plane. In FIG. 5c image 1 is in front, image 3 is in back, and image 2 is between images 1 and 3. The images have been translated in equal increments. That is, it is assumed that the images have been acquired with uniform spacing between the image planes, and it is further assumed that the images were acquired in parallel planes. It has been found that these assumptions make possible the rapid and simplified processing of planar images into three dimensional display will little or no noticeable effect on the three dimensional image presentation.

In FIG. 5b the same volumetric image information is presented as if the viewer has moved to his left while still viewing the scanned region from above. The view is as if the viewer is observing the region from a quadrant which is to the left of the volume's vertical center plane and above the volume's horizontal center plane. The images 1, 2, and 3 of FIG. 5b have been rotated as described in FIG. 3b and have correspondingly been translated in the horizontal direction as well as the previous vertical translation.

Figure 5D:
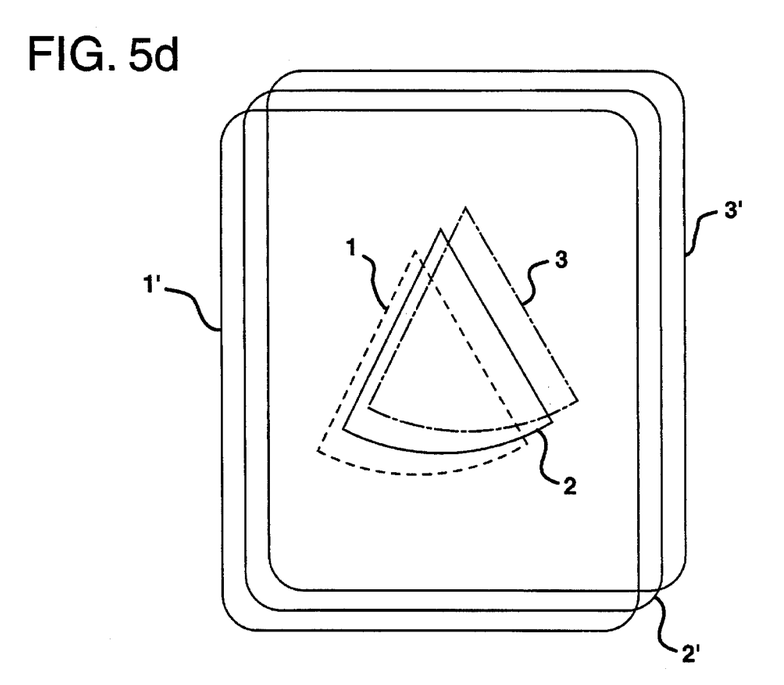

In FIG. 5d the scanned region is now viewed as if the observer has moved to his right and is viewing the region from the upper right quadrant of the horizontal and vertical center planes. The view is from a point angularly complementary to that of FIG. 5b but on the opposite side of the vertical plane. Thus, the images used in FIG. 5d are the same as those used in FIG. 5b by reason of the complementary angle of the view. The only difference between the two views of FIGS. 5b and 5d is the direction of the horizontal translation. In terms of processing differences, this is only a sign difference of the horizontal translation term.

Figure 6:
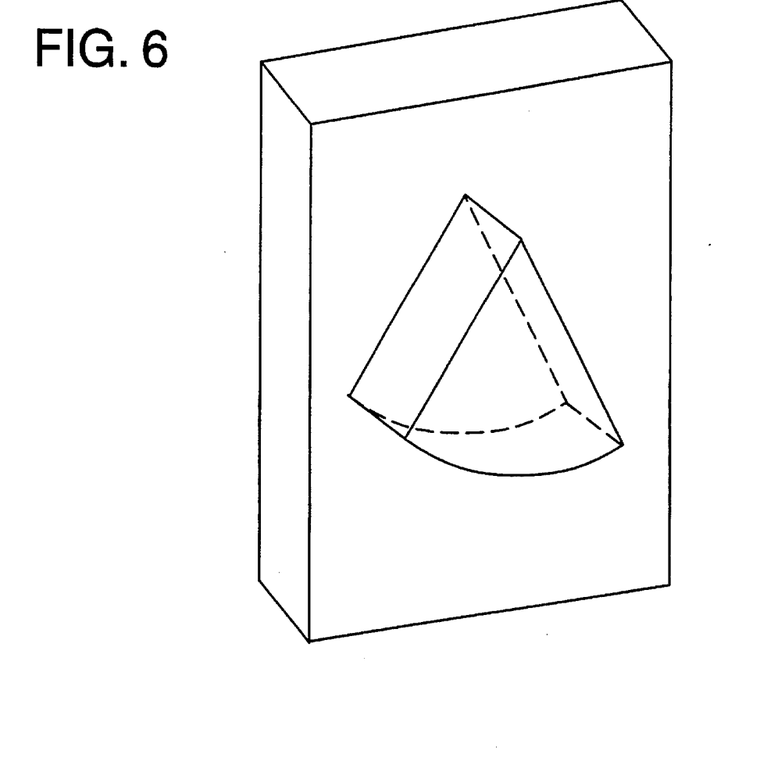
FIG. 6 illustrates a three dimensional sector image formed in accordance with the principles of the present invention.

The image information can be processed to produce a sequence of other combined images at viewing angles intermediate those of the views of FIGS. 5b, 5c, and 5d. Each view will have its own unique horizontal and vertical translation and sector angle, however, the sector angles used for the views between FIGS. 5b and 5c can be used with different horizontal translation between the views of FIGS. 5c and 5d. This sequence of views is stored in the image sequence memory 34 as each view is assembled and can be displayed in a real time sequence by recalling the sequence from the memory, moving back and forth through the sequence in time. The display will appear to be a three dimensional presentation of the scanned region which is rotating back and forth about its central vertical axis. By stopping the display sequence at a particular combined image the viewer will have the impression of viewing the scanned region from the perspective at which the sequencing was stopped. A detailed description of this display technique, including a preferred maximum intensity display technique, is found in the copending U.S. patent application mentioned above. The image frame and sector outline can be connected as shown in FIG. 6, giving an enhanced impression of a wedge shaped volume which is being turned about a central vertical axis.

There are a number of ways that the image information can be highlighted to further enhance the three dimensional presentation. One is to display the image by bringing forward the brightest voxel or volumetric display element in each path extending in the viewing direction into the region. The brightness of the brightest voxel is used on the display monitor. This maximum intensity display technique is described in the aforementioned copending U.S. patent application. Another technique is to highlight voxels closer to the front with greater brightness than voxels to the rear. This would means that the voxels of image 1 in FIGS. 5b–5d would be displayed brighter than those of images 2 and 3, for instance. A third highlighting technique is to highlight voxels on the side of the image "closer" to the viewer as compared to those on the side which is "further away" from the viewer. In FIG. 5b, for instance, this would mean that the voxels on the left side of the display would be relatively brighter than those on the right side. A smoothly varying function is used to modulate the brightness across the image, such as the cosine of the angle of the scan line with respect to a lateral side of the sector.

In the ultrasound system of FIG. 1 the sector information provided by the B mode processor 30, the velocity image processor 26, or the power image processor 28 is first converted into its conventionally proportioned image format as shown in FIG. 3a by the scan converter and display processor 32. This processing converts the polar coordinates of the sector scan into a system of Cartesian coordinates. The converted image information is then processed by rescaling as illustrated by FIGS. 3b–3d as required for the desired reproportioned image. When an original image is rotated about the y-axis, for instance, each point in the image moves in a horizontal plane. With the image initially converted to Cartesian coordinates, the y-axis rotation is afforded through a simple rescaling of the horizontal coordinates of the points in the image. The same result is obtained in the rotational processing of FIG. 3c by rescaling the original image in the vertical direction.

The present inventor has determined however that excellent three dimensional image presentations can be formed by performing coordinate conversion directly on initially received polar coordinate image data without the initial conversion into Cartesian coordinates. That is, the sector information provided by the B mode processor 30, the velocity image processor 26, or the power image processor 28 is converted directly into its final scaled sector angle format by rescaling the angle of each scan line in the scan converter and display processor 32. The effective result is that, instead of effecting a pure horizontal (or vertical) relocation of the image points, the image points move from their original scan lines to those of the new sector angle by effectively following their arcs of equidistance from the image apex. This is indicated in FIG. 3b by the arcuate arrows 81 and in FIG. 3c by arcuate arrows 91, for instance. Because the scan lines data is relocated arcuately rather than horizontally a slight radial error in point position occurs as shown in FIG. 3b. This effect can be compensated for by concurrently compressing the scan line data radially as the arc of the sector is reduced; the greater the sector arc reduction, the greater the reduction of the scan line length. One technique is to halve the difference between the locations of the sector corners if relocated horizontally as compared to arcuately. This single processing technique for polar coordinates obviates the need for the initial Cartesian conversion process and shortens the time required to form three dimensional images without noticeably degrading the image presentation.

Since the linear scanned information of FIGS. 4a–4c is in a system of Cartesian coordinates from the outset, accurate axial rotations are effected directly in a single processing step as shown by horizontal and vertical arrows 181 and 191. In FIG. 4b the image scan line spacing is rescaled in the horizontal direction and in FIG. 4c the scan line data is rescaled in the vertical direction. Translation is afforded in the same manner as for the sector images, as a function of the assumed or measured interplane spacing and the viewing angle of the viewer.

What is claimed is:

1. A method for producing a perspective view of a volumetric region of the body from a plurality of spatially related planar ultrasonic sector images comprising the steps of:

receiving a plurality of spatially related ultrasonic sector images from said volumetric region;

identifying the angle of said perspective view in relation to a reference plane;

processing each image by a) scaling one or more of the dimensions of said image in proportion to said perspective viewing angle, and b) translating the image in the plane of the image in proportion to the spacing between said spatially related planes and said perspective viewing angle;

combining said processed images to form a composite perspective view image; and displaying said perspective view image.

2. The method of claim 1, further comprising the step of repeating said identifying, processing, and combining steps a number of times, each for a different perspective viewing angle; and wherein said displaying step comprises the step of displaying a sequence of said composite perspective view images.

3. The method of claim 2, wherein said displaying step comprises the step of displaying said sequence of composite perspective view images in a sequence order which is in the order of increasing or decreasing perspective viewing angle.

4. The method of claim 1, wherein said processing step of scaling comprises the step of reducing the horizontal dimension of said image in proportion to said perspective viewing angle; and wherein said processing step of translating comprising the step of translating the image in the horizontal direction.

5. The method of claim 4, further comprising the step of repeating said identifying, processing, and combining steps a number of times, each for a different perspective viewing angle; and wherein said displaying step comprises the step of displaying a sequence of said composite perspective view images.

6. The method of claim 1, wherein said processing step of scaling comprises the step of reducing the vertical dimension of said image in proportion to said perspective viewing angle; and wherein said processing step of translating comprising the step of translating the image in the vertical direction.

7. The method of claim 6, further comprising the step of repeating said identifying, processing, and combining steps a number of times, each for a different perspective viewing angle; and wherein said displaying step comprises the step of displaying a sequence of said composite perspective view images.

8. The method of claim 1, wherein said received ultrasonic sector images each exhibit a given angle of sector; and wherein said processing step of scaling comprises the step of reducing the angle of said sectors in relation to said perspective viewing angle; and wherein said processing step of translating comprising the step of translating the image in the horizontal direction.

9. The method of claim 8, further comprising the step of repeating said identifying, processing, and combining steps a number of times, each for a different perspective viewing angle; and wherein said displaying step comprises the step of displaying a sequence of said composite perspective view images.

10. The method of claim 1, wherein said received ultrasonic sector images each exhibit a given angle of sector; and wherein said processing step of scaling comprises the step of increasing the angle of said sectors and decreasing the radial depth of said sectors in relation to said perspective viewing angle; and wherein said processing step of translating comprising the step of translating the image in the vertical direction.

11. The method of claim 10, further comprising the step of repeating said identifying, processing, and combining steps a number of times, each for a different perspective viewing angle; and wherein said displaying step comprises the step of displaying a sequence of said composite perspective view images.

12. An ultrasonic imaging system which produces a perspective view of a volumetric region of the body from an ultrasonic sector image comprising:

an ultrasonic probe for receiving a plurality of spatially related ultrasonic echo information signals from scan lines of a sector image plane intersecting said volumetric region;

means for identifying the angle of said perspective view in relation to a reference plane;

a scan converter for processing said spatially related ultrasonic echo information signals by a) scaling one or more of the dimensions of said sector image in proportion to said perspective viewing angle, and b) translating the sector image in the plane of the image in proportion to said perspective viewing angle; and a display which displays said scaled and translated sector image.

13. The ultrasonic imaging system of claim 12, wherein said ultrasonic probe further comprises means for receiving a plurality of spatially related ultrasonic echo information signals from scan lines of a plurality of spatially related sector image planes intersecting said volumetric region;

wherein said scan converter comprises means for processing the echo information signals of each sector image by a) scaling one or more of the dimensions of said image in proportion to said perspective viewing angle, and b) translating the image in the plane of the image in proportion to the spacing between said spatially related sector image planes and said perspective viewing angle; and further comprising:

an image combiner for combining said processed sector images to form a composite perspective view image; and wherein said display comprises means for displaying said perspective view image.

14. The ultrasonic imaging system of claim 12, wherein said means for identifying comprises means for identifying the angles of a plurality of perspective views in relation to a reference plane; and further comprising:

a controller, coupled to said scan converter, for controlling said scan converter to process said spatially related ultrasonic echo information signals by a) scaling one or more of the dimensions of said sector image in proportion to each of said perspective viewing angles, and b) translating the sector image in the plane of the image in proportion to each of said perspective viewing angles; and wherein said display comprises means for displaying a scaled and translated sector image for each of said viewing angles.

15. The ultrasonic imaging system of claim 14, wherein said ultrasonic probe further comprises means for receiving a plurality of spatially related ultrasonic echo information signals from scan lines of a plurality of spatially related sector image planes intersecting said volumetric region;

wherein said controller comprises means for controlling said scan converter to process the echo information signals of each sector image plane by a) scaling one or more of the dimensions of each image in proportion to each of said perspective viewing angles, and b) translating each image in the plane of the image in proportion to the spacing between said spatially related sector image planes and a perspective viewing angle; and further comprising:

an image combiner for combining said processed sector images on the basis of each perspective viewing angle to form a sequence of composite perspective view images; and wherein said display comprises means for displaying said sequence of composite perspective view images.

16. The ultrasonic imaging system of claim 15, wherein said display comprises means for displaying said sequence of composite perspective view images in the order of increasing or decreasing perspective view angle.

17. The ultrasonic imaging system of claim 12, wherein said scan converter comprises a scan converter which processes said spatially related ultrasonic echo information signals by a) reducing the horizontal dimension of said sector image, and b) translating the sector image in the horizontal direction.

18. The ultrasonic imaging system of claim 12, wherein said scan converter comprises a scan converter which processes said spatially related ultrasonic echo information signals by a) reducing the arc of said sector image, and b) translating the sector image in the horizontal direction.

19. The ultrasonic imaging system of claim 12, wherein said scan converter comprises a scan converter which processes said spatially related ultrasonic echo information signals by a) reducing the vertical dimension of said sector image, and b) translating the sector image in the vertical direction.

20. The ultrasonic imaging system of claim 12, wherein said scan converter comprises a scan converter which processes said spatially related ultrasonic echo information signals by a) increasing the arc and decreasing the radial depth of said sector image, and b) translating the sector image in the vertical direction.

21. The ultrasonic imaging system of claim 12, wherein said scan converter comprises a scan converter which processes said spatially related ultrasonic echo information signals by a) reducing the arc and decreasing the radial dimension of said sector image, and b) translating the sector image in the horizontal direction.

22. An ultrasonic imaging system which produces a perspective view of a volumetric region of the body from an ultrasonic image of parallel scan lines comprising:

an ultrasonic probe for receiving a plurality of spatially related ultrasonic echo information signals from substantially parallel scan lines of an image in a plane intersecting said volumetric region;

means for identifying the angle of said perspective view in relation to a reference plane;

a scan converter for processing said spatially related ultrasonic echo information signals by a) scaling one or more of the dimensions of said image in proportion to said perspective viewing angle, and b) translating the image in the plane of the image in proportion to said perspective viewing angle; and a display which displays said scaled and translated image.

23. The ultrasonic imaging system of claim 22, wherein said scan converter comprises a scan converter which processes said spatially related ultrasonic echo information signals by a) reducing the horizontal dimension of said image, and b) translating the image in the horizontal direction.

24. The ultrasonic imaging system of claim 22 wherein said scan converter comprises a scan converter which processes said spatially related ultrasonic echo information signals by a) reducing the vertical dimension of said image, and b) translating the image in the vertical direction.

* * * * *